US006558701B2

(12) United States Patent
Bartholomaeus et al.

(10) Patent No.: US 6,558,701 B2
(45) Date of Patent: May 6, 2003

(54) MULTILAYER TABLET FOR ADMINISTERING A FIXED COMBINATION OF TRAMADOL AND DICLOFENAC

(75) Inventors: Johannes Bartholomaeus, Aachen (DE); Iris Ziegler, Rott-Roetgen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/016,121

(22) Filed: Dec. 17, 2001

(65) Prior Publication Data

US 2002/0132850 A1 Sep. 19, 2002

Related U.S. Application Data

(63) Continuation of application No. PCT/EP00/05385, filed on Jun. 13, 2000.

(30) Foreign Application Priority Data

Jun. 17, 1999 (DE) .......................................... 199 27 688

(51) Int. Cl.$^7$ .............................. A61K 9/22; A61K 9/24; A61K 9/26; A61K 9/32; A61K 9/36
(52) U.S. Cl. .................. 424/472; 424/468; 424/469; 424/474; 424/480; 424/482; 514/772.3; 514/781; 514/784; 514/786
(58) Field of Search ................................. 424/472, 468, 424/473, 489, 469, 474, 480, 482

(56) References Cited

U.S. PATENT DOCUMENTS 6,419,957 B1 * 7/2002 Lenaerts et al. ............ 424/488

* cited by examiner

Primary Examiner—James M. Spear
(74) Attorney, Agent, or Firm—Crowell & Moring LLP

(57) ABSTRACT

A multilayer tablet for oral administration containing at least one Tramadol layer including Tramadol or a physiologically acceptable salt thereof; at least one diclofenac layer including diclofenac or a physiologically acceptable salt thereof, and at least one separating layer which separates the tramadol layer(s) and the diclofenac layer(s) from each other.

45 Claims, 3 Drawing Sheets

MULTILAYER TABLET FOR ADMINISTERING A FIXED COMBINATION OF TRAMADOL AND DICLOFENAC

CROSS REFERENCE TO RELATED APPLICATIONS

This application is a continuation of international patent application no. PCT/EP00/05385, filed Jun. 13, 2000, designating the United States of America, the entire disclosure of which is incorporated herein by reference. Priority is claimed based on Federal Republic of Germany patent application no. DE 199 27 688.9, filed Jun. 17, 1999.

BACKGROUND OF THE INVENTION

The present invention relates to a multilayer tablet containing the active substances Tramadol and Diclofenac and/or their in each case physiologically compatible salts, with the active substances being separated from one another by a separating layer.

Tramadol is an analgesic used to treat severe and moderately severe pain, whose mode of action is not based on a pure opioid mechanism. Tramadol does not exhibit the characteristic side effects of an opioid. In some cases nausea is observed as an undesirable accompanying symptom.

Other known, non-opioid analgesics suitable for treating less severe pain include steroid-free analgesics such as Diclofenac-Na, acetylsalicylic acid or Ibuprofen.

Furthermore, for the treatment of moderate to severe pain, the World Health Organization (WHO) recommends combining opioid analgesics with non-steroidal analgesics in order to produce a more effective pain relief and possibly reduce amounts of analgesic which are necessary to administer.

Raffa, European Patent no. EP-B 546 676 discloses, for example, that the combination of Tramadol-HCl with non-steroidal anti-inflammatories, such as for example Ibuprofen, in a composition ratio of 1:1 to 1:200 produces a synergistically enhanced analgesic action and reduces the undesired accompanying symptoms. Tramadol-HCl and Diclofenac-Na form a sparingly soluble compound however. It is therefore to be expected that the bioavailability of the two active substances is reduced and that higher dosages are required in order to compensate for this.

SUMMARY OF THE INVENTION

The object of the present invention was accordingly to combine the two active substances Tramadol and Diclofenac and/or physiologically compatible salts thereof, respectively, in a common administration unit without however impairing the release profiles of the two active substances or reducing their bioavailability.

This object is achieved in accordance with the invention by providing a multilayer tablet to be administered orally that contains in at least one layer Tramadol and/or a physiologically compatible salt thereof and in at least one further layer Diclofenac and/or a physiologically compatible salt thereof, with a separating layer being present in each case between the layers containing the active substances.

Preferably the tablet consists of seven layers, particularly preferably of five layers and most particularly preferably of three layers.

Preferred physiologically compatible salts of Tramadol include Tramadol hydrochloride, Tramadol hydrobromide, Tramadol sulfate, Tramadol phosphate, Tramadol fumarate, Tramadol succinate, Tramadol maleate, Tramadol nitrate, Tramadol acetate, Tramadol propionate, Tramadol malonate, Tramadol citrate, Tramadol tartrate, Tramadol benzoate, Tramadol salicylate, Tramadol phthalate and/or Tramadol nicotinate. Particularly preferably Tramadol hydrochloride is used.

Preferred physiologically compatible salts of Diclofenac include Diclofenac-sodium, Diclofenac-potassium, Diclofenac-calcium, Diclofenac-magnesium and/or Diclofenac-cholestyramine. Particularly preferably Diclofenac-sodium is used.

The multilayer tablet to be used according to the invention may contain the conventional auxiliary substances and additives in the Tramadol-containing layer as well as in the Diclofenac-containing layer.

Preferably the multilayer tablet includes one or more layers each respectively containing one of the two active substances, preferably uniformly divided, in a retarding (delayed release) matrix, whereby optimal, individually matched release values can be achieved. By combination with the immediately released active substance an initial dose for a rapid pain relief can be achieved. The slow release from the retarded form permits the maintenance of therapeutic blood levels over an extended time.

The layers may also contain a retarded, particulate form of the respective active substance, preferably granules and/or pellets, particularly preferably pellets produced by extrusion and/or spheronisation. Particularly preferably in this connection the release of the active substance or active substances will be adjusted so that the tablet has to be administered at most twice, and preferably only once per day.

The proportion of the two analgesics in relation to auxiliary substances in the multilayer tablet may be adjusted depending on the desired release duration and amount of the analgesics to be released. Preferably the content of Tramadol is 2 to 60 wt. %, more preferably 5 to 45 wt. %, and most particularly preferably 10 to 35 wt. %, relative to the total weight of the multilayer tablet. Preferably the proportion of Diclofenac is 2 to 30 wt. %, particularly preferably 5 to 25 wt. %, and most particularly preferably 6 to 20 wt. %, relative to the total weight of the multilayer tablet. Based on the known activities of the analgesics, persons skilled in the art know what quantitative ratios of these analgesics should be used in order to achieve the desired effect of the active substances.

Suitable matrix materials useful in the invention include physiologically compatible, hydrophilic materials that are known to persons skilled in the art. Preferred hydrophilic matrix materials include polymers, particularly preferably cellulose ethers, cellulose esters and/or acrylic resins. Most particularly preferred matrix materials include ethylcellulose, hydroxypropylcellulose, hydroxypropylmethylcellulose, hydroxymethylcellulose, poly(meth)acrylic acid and/or derivatives thereof such as its salts, amides or esters.

Particularly preferably there is used as physiologically compatible material for a retarding matrix at least one cellulose ether and/or cellulose ester whose 2 wt. % aqueous solution at 20° C. has a viscosity of 3,000 to 150,000 mP·as, preferably 10,000 to 150,000 mP·as, optionally in combination with a filler that is not swellable in an aqueous medium, such as for example calcium hydrogen phosphate, or with an insoluble filler that is swellable in an aqueous medium, such as for example microcrystalline cellulose, or a filler that is soluble in aqueous media, such as for example lactose.

Also preferred is a matrix material of hydrophobic materials such as hydrophobic polymers, waxes, fats, long-chain fatty acids, fatty alcohols or corresponding esters or ethers or their mixtures. Particularly preferably monoglycerides or diglycerides of $C_{12}$–$C_{30}$ fatty acids and/or $C_{12}$–$C_{30}$ fatty alcohols and/or waxes or their mixtures are used as hydrophobic materials.

It is also possible to use mixtures of the aforementioned hydrophilic and hydrophobic materials as a retarding matrix material.

In one preferred embodiment the separating layer is slightly permeable with respect to the two active substances also on contact with aqueous body fluids. This separating layer is preferably composed of a polymer, a wax, a fat, a fatty acid, a fatty alcohol or a corresponding ether or ester or a mixture thereof, and has a melting point of $\geq 40°$ C.

Preferred physiologically compatible polymers which may be used in the invention include cellulose acetate, ethylcellulose, cellulose butyrate, polyethylene or ethylene/vinyl acetate copolymers.

In a further preferred embodiment the separating layer is more specifically readily permeable with respect to the two active substances per se on contact with aqueous body fluids, the thickness of the separating layer then being adjusted however so that the two active substances do not come into contact with one another during the duration of the release.

To this end a permeable separating layer of the tablet may consist of hydroxypropylmethylcellulose, hydroxyethylcellulose, hydroxymethylcellulose and/or hydroxypropylcellulose.

Furthermore the separating layer as well as the active substance-containing layers may include further auxiliary substances and additives. These may be fillers, preferably lactose, microcrystalline cellulose or calcium hydrogen phosphate, or slip agents, lubricants and/or flow regulating agents and/or plasticisers, preferably highly dispersed silicon dioxide, talcum, magnesium stearate and/or stearic acid.

The individual layers of the multilayer tablet according to the invention may also be formulated so that they separate from one another on contact with aqueous body fluids and thus release the active substances in a spatially separated manner. As physiologically compatible release agents that release the layers from one another on contact with aqueous body fluids, there may be used Crospovidon, Croscarmelose, sodium starch glycolate, starch and/or hydroxypropylcellulose having a low degree of substitution.

The present invention accordingly provides multilayer tablets that contain at least one release layer that effects a separation of the different layers from one another on contact with aqueous body fluids. It is however also possible for the layers to remain combined with one another on contact with aqueous body fluids and to release the active substances, separated by the separating layer, independently of one another.

With the multilayer tablet according to the invention a controlled release of both active substances can also be achieved by means of a coating that permits a controlled, as a rule delayed, release of the active substance in an aqueous medium. Suitable retard coatings include water-insoluble waxes or polymers, such as for example acrylic resins, preferably poly(meth)acrylates, or water-insoluble celluloses such as ethylcellulose. These materials are known from the prior art, e.g. Bauer, Lehmann, Osterwald, Rothgang " Überzogene Arzneiformen" ("Coated Medicament Forms"), Wissenschaftliche Verlagsgesellschaft mbH Stuttgart, 1988, p. 69 ff. They are introduced here by way of reference.

In addition to the water-insoluble polymers, in the coating there optionally may also be used non-retarded, preferably water-soluble, polymers in order to adjust the release rate of the active substance, in amounts of up to 30 wt. %, such as polyvinylpyrrolidone or water-soluble celluloses, preferably hydroxypropyl-cellulose, hydroxypropylmethylcellulose or, or water-soluble pore-forming agents such as, for example, lactose, NaCl, sucrose, and/or known plasticisers.

In addition to the retarding coating, the multilayer tablet according to the invention may also be provided with further coatings. One such further coating may for example dissolve in a manner dependent on the pH value. In this way a specific amount of active substance can pass undissolved through the stomach and be released only in the intestinal tract.

The multilayer tablet according to the invention may also have at least one score mark that enables the dose being administered to be subdivided, preferably halved. This permits the dosage to be matched to the individual requirements of the patient, corresponding to the amount of the analgesics to be administered individually.

The invention accordingly also provides multilayer tablets that have at least one score mark that enables the tablet to be subdivided, preferably halved.

The multilayer tablets are produced according to known methods, such as are described for example in R. Voigt, "Lehrbuch der pharmazeutischen Technologie", 6$^{th}$ Edition, p. 225 ff. They are introduced here by way of reference.

Preferably the production of the multilayer tablets is carried out by combining the constituents of the individual layers first of all separately by mixing the individual constituents in a mixer, optionally followed by granulation. The different layers are then compressed in succession in a tablet press, preferably in a rotary pelleting machine to form a tablet, in such a way that the separating layer prevents the active substance-containing layers from coming in contact with one another.

The multilayer tablets according to the invention may be of the usual shapes and sizes. If the multilayer tablet according to the invention contains coatings, then these may be applied by conventional processes, such as for example dragée coating, spraying of solutions, dispersion or suspensions, by melt processes or by powder application processes.

If the multilayer tablet according to the invention is intended to be administered twice a day, the release profile for the active substance Tramadol from the multilayer tablet according to the invention is preferably controlled so that the released amount of Tramadol in percent referred to the total amount is 2 to 40%, preferably 5 to 30% after 30 minutes, 5 to 80%, preferably 20 to 60% after 120 minutes, 30 to 90%, preferably 35 to 75% after 240 minutes, 50 to 95%, preferably 60 to 90% after 360 minutes, 60 to 100%, preferably 70 to 100% after 480 minutes, and 70 to 100%, preferably 75 to 100% after 600 minutes.

The release profile for the active substance Tramadol from the multilayer tablet according to the invention for once daily administration is preferably controlled so the released amount of Tramadol in percent, relative to the total amount, is 2 to 40%, preferably 5 to 30% after 60 minutes, 5 to 80%, preferably 20 to 60% after 240 minutes, 30 to 90%, preferably 35 to 75% after 480 minutes, 50 to 95%, preferably 60 to 90% after 720 minutes, 60 to 100%, preferably 70 to 100% after 960 minutes, and 70 to 100%, preferably 75 to 100% after 1200 minutes.

The release profile for the active substance Diclofenac from the multilayer tablet according to the invention for a twice daily administration is preferably controlled so that so that the released amount of Diclofenac in percent referred to the total amount is 0% after 30 minutes, ≦5% after 120 minutes, 5 to 50%, preferably 10 to 35% after 240 minutes, 30 to 95%, preferably 35 to 80% after 480 minutes, and 45 to 100%, preferably 60 to 100% after 600 minutes.

The release profile for the active substance Diclofenac from the multilayer tablet according to the invention for once daily administration is preferably controlled so that the released amount of Diclofenac in percent relative to the total amount is ≦5% after 120 minutes, 5 to 40%, preferably 10 to 30% after 240 minutes, 15 to 60%, preferably 15 to 50% after 480 minutes, 30 to 80%, preferably 35 to 80% after 720 minutes, and 50 to 100%, preferably 60 to 100% after 1,200 minutes.

The present invention accordingly provides multilayer tablets that are characterized in that in the case of twice daily administration, ≧70% of the Tramadol and ≧60% of the Diclofenac, respectively, are released within 8 hours. The invention furthermore provides multilayer tablets that are characterised in that in the case of once daily administration, ≧70% of the Tramadol and ≧60% of the Diclofenac, respectively, are released within 16 hours. With gastric juice-resistant tablets, the aforementioned release profiles with regard to the Tramadol release times as well as the residence time in the stomach should be appropriately readjusted.

BRIEF DESCRIPTION OF THE DRAWINGS

The invention will be described in further detail with reference to examples and the accompanying drawings in which.

DETAILED DESCRIPTION OF THE EXAMPLES

Figure 1:
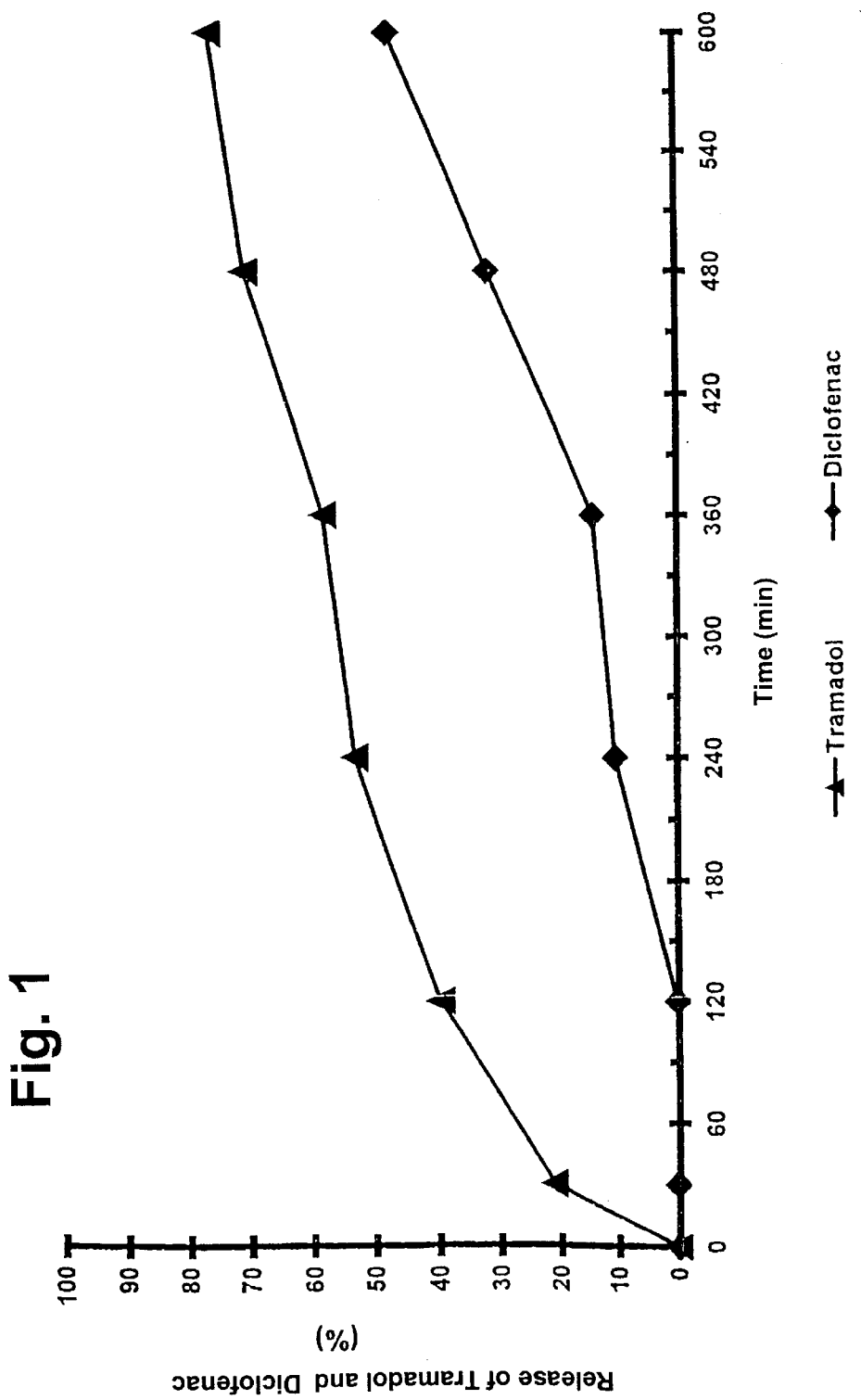
FIG. 1 is a graph showing the release of tramadol and diclofenac from a first tablet over time.

The release profiles of the multilayer tablets according to the invention were determined as follows:

The tablets according to the invention were added to 600 ml of enzyme-free artificial gastric juice (pH 1.2) in a release apparatus equipped with a paddle stirrer according to the European Pharmacopoeia at a temperature of the release medium of 37° C. and a rotational speed of the paddle stirrer of 75 m$^{-1}$, for 2 hours. The preparations were then treated for a further 8 hours in 900 ml of enzyme-free artificial intestinal juice (pH 7.2). The amount of the respective active substance Tramadol or Diclofenac released in each case over time is determined by HPLC. The illustrated values and curves are the mean values of in each case 6 samples. The following examples serve to illustrate the invention further without however restricting the general inventive concept.

EXAMPLE 1

The layers of the multilayer tablet according to the invention were first produced individually. For this purpose the active substance layer containing Tramadol hydrochloride was prepared by mixing Tramadol hydrochloride, microcrystalline cellulose, hydroxypropyl-methylcellulose, highly dispersed silicon dioxide and magnesium stearate in a cube mixer. The separating layer was prepared by mixing microcrystalline cellulose, hydroxypropylmethylcellulose, highly dispersed silicon dioxide and magnesium stearate in a cube mixer. The active substance layer containing Diclofenac-Na was prepared by mixing micronised Diclofenac-Na, microcrystalline cellulose, hydroxypropylmethylcellulose, highly dispersed silicon dioxide and magnesium stearate in a cube mixer. The two layers containing the active substances together with the interposed separating layer were then compressed in one work stage to form a three-layer tablet having a diameter of 12 mm. For this purpose the successive layer amounts were respectively lightly compressed in a matrix using an eccentric tableting machine, following which the whole layer sequence was compressed. The tablet had a hardness of 100 to 130 N according to the Erweka breaking resistance tester.

Composition of the 3-layer tablet

| | | |
|---|---|---|
| Tramadol hydrochloride | 100.00 mg | |
| Microcrystalline cellulose (Avicel PH 101, FMC) | 82.00 mg | |
| Hydroxypropylmethylcellulose, 100,000 mP · as (Metolose 90 SH 100,000, ShinEtsu) | 63.00 mg | |
| Highly dispersed silicon dioxide (Aerosil, Degussa) | 2.50 mg | |
| Magnesium stearate | 2.50 mg | 1st layer: 250 mg |
| Microcrystalline cellulose (Avicel PH 101, FMC) | 71.00 mg | |
| Hydroxypropylmethylcellulose, 100,000 mP · as (Metolose 90 SH 100,000, ShinEtsu) | 27.00 mg | |
| Highly dispersed silicon dioxide (Aerosil, Degussa) | 1.00 mg | |
| Magnesium stearate | 1.00 mg | Separating layer: 100 mg |
| Diclofenac-Na, micronised | 50.00 mg | |
| Microcrystalline cellulose (Avicel PH 101, PMC) | 132.00 mg | |
| Hydroxypropylmethylcellulose, 100,000 mP · as (Metolose 90 SH 100,000, ShinEtsu) | 63.00 mg | |

| | |
|---|---|
| Highly dispersed silicon dioxide (Aerosil, Degussa) | 2.50 mg |
| Magnesium stearate | 2.50 mg 3rd layer: 250 mg |
| Total | 600.00 mg |

The release profile was as follows and is shown in FIG. 1:

| | Released Fraction in % | |
|---|---|---|
| Time in mins. | Diclofenac | Tramadol |
| 30 | 0 | 21 |
| 120 | 0 | 40 |
| 240 | 11 | 54 |
| 360 | 14 | 59 |
| 480 | 32 | 72 |
| 600 | 48 | 77 |

Figure 2:
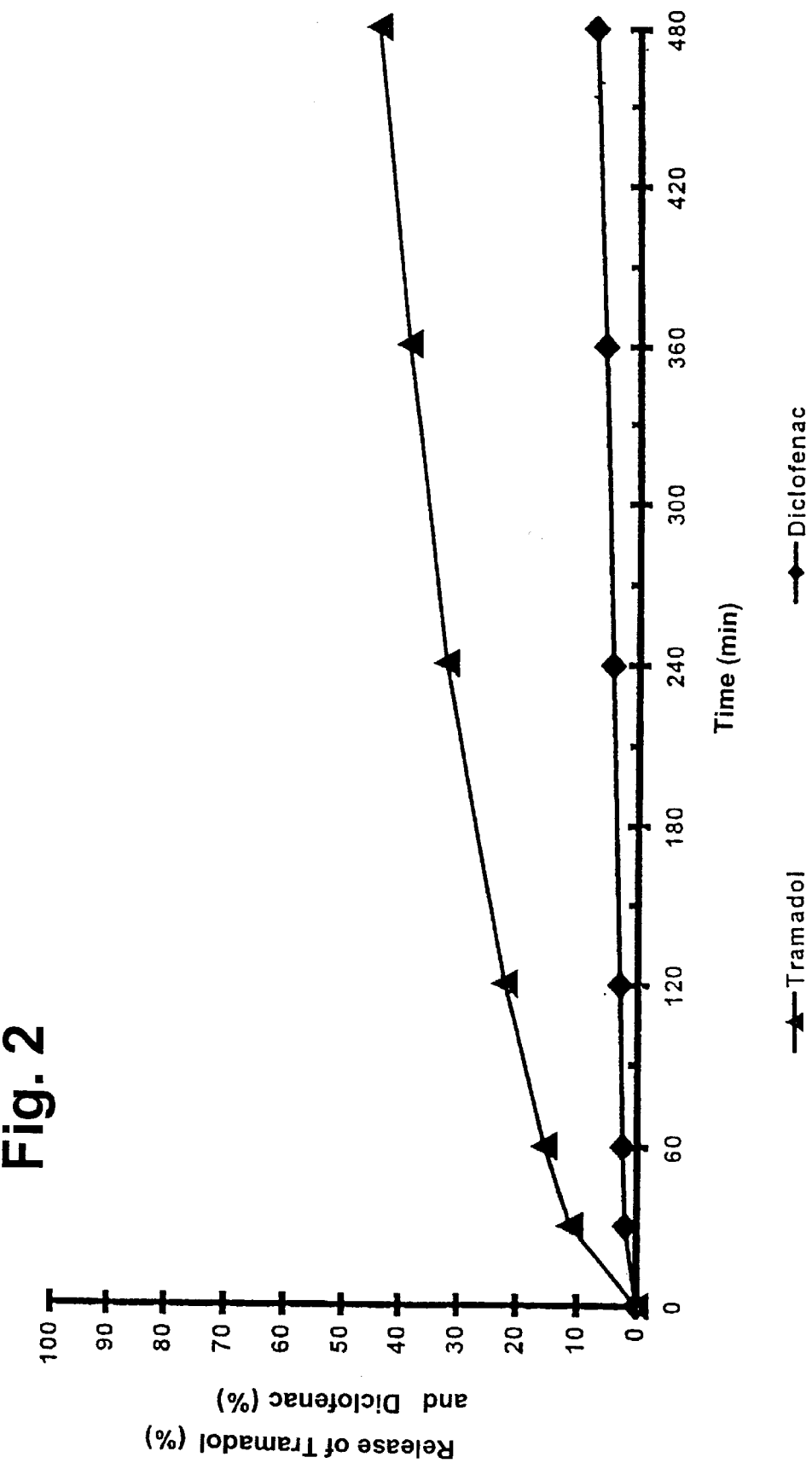
FIG. 2 is a graph showing the release of tramadol and diclofenac from a second tablet over time.

FIG. 2 shows the release profile of a matrix tablet having a diameter of 12 mm and containing 100 mg of Tramadol and 50 mg of Diclofenac compressed jointly in a hydrophilic matrix of hydroxypropylmethylcellulose. A comparison of FIGS. 1 and 2 shows that the amounts of the active substances Tramadol and Diclofenac released from the three-layer tablet according to the invention after 8 hours are substantially larger than the release from the so-called joint matrix tablets.

Figure 3:
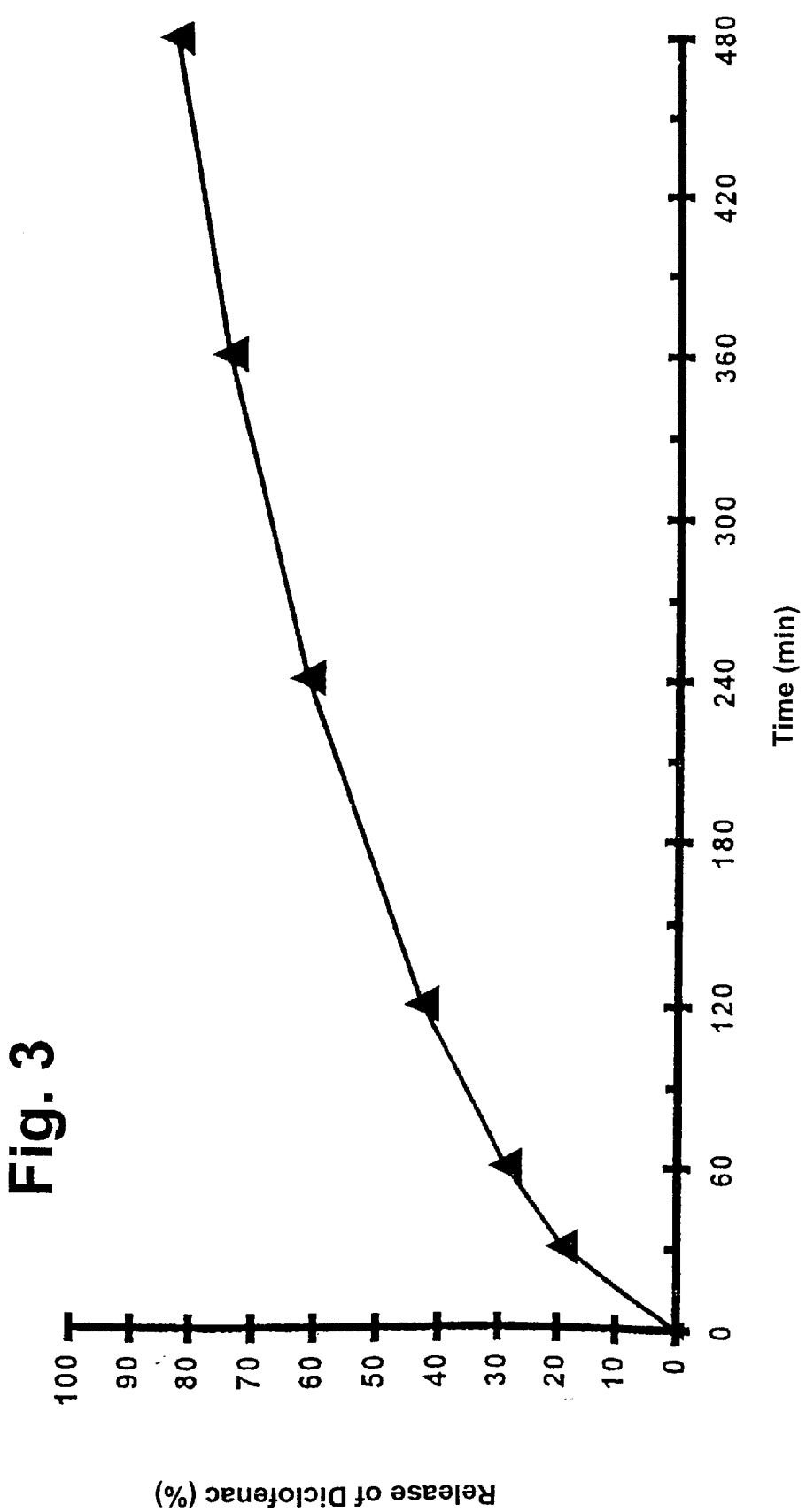
FIG. 3 is a graph showing the release of tramadol and diclofenac from a third tablet over time.

FIG. 3 shows the release profile of retarded matrix tablets having a diameter of 10 mm containing as active substance only 100 mg of Tramadol in a hydrophilic matrix consisting of hydroxypropylmethylcellulose. A comparison of FIGS. 1 and 3 shows that the amounts of Tramadol released from the three-layer tablets according to the invention ($\geq 75\%$) correspond to the release from the Tramadol tablets per se ($\geq 80\%$).

EXAMPLE 2

The preparation of the individual layers was carried out in a similar manner to Example 1. The two active substance-containing layers together with the interposed separating layer were then compressed in a similar manner to form a 3-layer tablet of diameter 16 mm.

Composition of the 3-layer tablet

| | |
|---|---|
| Tramadol hydrochloride | 100.00 mg |
| Microcrystalline cellulose (Avicel PH 101, FMC) | 82.00 mg |
| Hydroxypropylmethylcellulose, 100,000 mP · as (Metolose 90 SH 100,000, ShinEtsu) | 63.00 mg |
| Highly dispersed silicon dioxide (Aerosil, Degussa) | 2.50 mg |
| Magnesium stearate | 2.50 mg 1st layer: 250 mg |
| Microcrystalline cellulose (Avicel PH 101, FMC) | 94.00 mg |
| Crosslinked polyvinyl-pyrrolidone (Kollidon CL, BASF) | 5.00 mg |
| Magnesium stearate | 1.00 mg Separating layer: 100 mg |
| Diclofenac-Na, micronised | 50.00 mg |
| Microcrystalline cellulose | 132.00 mg |
| (Avicel PH 101, FMC) | |
| Hydroxypropylmethylcellulose, 100,000 mP · as (Metolose 90 SH 100,000, ShinEtsu) | 63.00 mg |
| Highly dispersed silicon dioxide (Aerosil, Degussa) | 2.50 mg |
| Magnesium stearate | 2.50 mg 3rd layer: 250 mg |
| Total | 600.00 mg |

The release profile was as follows:

| | Released Fraction in % | |
|---|---|---|
| Time in mins. | Diclofenac | Tramadol |
| 30 | 0 | 35 |
| 120 | 0 | 71 |
| 240 | 14 | 85 |
| 360 | 18 | 90 |
| 480 | 37 | 95 |
| 600 | 56 | 99 |

EXAMPLE 3

Tramadol hydrochloride and Diclofenac-Na were in each case mixed in a similar manner to Example 1 with microcrystalline cellulose, hydroxypropylmethylcellulose, highly dispersed silicon dioxide and magnesium stearate in a suitable mixer and were then compressed in a suitable tableting press together with an active substance-free intermediate layer of microcrystalline cellulose, crosslinked polyvinylpyrrolidone and magnesium stearate to form 3-layer tablets of size 7 mm×14 mm with a score mark. The tablets have a hardness of 100–130 N.

Composition of the 3-layer tablet

| | |
|---|---|
| Tramadol hydrochloride | 100.00 mg |
| Microcrystalline cellulose (Avicel PH 101, FMC) | 82.00 mg |
| Hydroxypropylmethylcellulose, 100,000 mP · as (Metolose 90 SH 100,000, ShinEtsu) | 63.00 mg |
| Highly dispersed silicon dioxide (Aerosil, Degussa) | 2.50 mg |
| Magnesium stearate | 2.50 mg 1st layer: 250 mg |
| Microcrystalline cellulose (Avicel PH 101, FMC) | 94.00 mg |
| Crosslinked polyvinyl-pyrrolidone (Kollidon CL, BASF) | 5.00 mg |
| Magnesium stearate | 1.00 mg Separating layer: 100 mg |
| Diclofenac-Na, micronised | 50.00 mg |
| Microcrystalline cellulose (Avicel PH 101, FMC) | 132.00 mg |
| Hydroxypropylmethylcellulose, 100,000 mP · as (Metolose 90 SH 100,000, ShinEtsu) | 63.00 mg |
| Highly dispersed silicon dioxide (Aerosil, Degussa) | 2.50 mg |
| Magnesium stearate | 2.50 mg 3rd layer: 250 mg |
| Total | 600.00 mg |

The release profile was determined similarly to Example 1 and is shown in the following Table, the individual layers of the tablet dissociating from one another during the course of the first few hours of the release process and then in each case being present as separate units in the release apparatus and released.

| Time in mins. | Released Fraction in % | |
|---|---|---|
| | Diclofenac | Tramadol |
| 30 | 0 | 22 |
| 120 | 0 | 45 |
| 240 | 15 | 60 |
| 360 | 31 | 70 |
| 480 | 50 | 80 |
| 600 | 72 | 96 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A multilayered tablet comprising a Tramadol layer which contains Tramadol or a pharamaceutically acceptable salt thereof, a Diclofenac layer which contains Diclofenac or a pharmaceutically acceptable salt thereof, and a separating layer which separates the Tramadol layer from the Diclofenac layer.

2. The multilayered tablet according to claim 1, wherein the Tramadol layer comprises a pharamaceutically acceptable salt of Tramadol selected from the group consisting of Tramadol hydrochloride, Tramadol hydrobromide, Tramadol sulfate, Tramadol phosphate, Tramadol fumarate, Tramadol succinate, Tramadol maleate, Tramadol nitrate, Tramadol acetate, Tramadol propionate, Tramadol malonate, Tramadol citrate, Tramadol tartrate, Tramadol benzoate, Tramadol salicylate, Tramadol phthalate and Tramadol nicotinate, and the Diclofenac layer comprises a pharmcologically acceptable salt of Diclofenac selected from the group consisting of Diclofenac-sodium, Diclofenac-potassium, Diclofenac-calcium, Diclofenac-magnesium and Diclofenac-cholestyramine.

3. The multilayered tablet of claim 2, wherein the Tramadol layer comprises Tramadol-HCl.

4. The multilayered tablet of claim 2, wherein Diclofenac layer comprises Diclofenac-Na.

5. The multilayered tablet of claim 1, comprising at least five layers.

6. The multilayered tablet of claim 5, comprising at least seven layers.

7. The multilayered tablet of claim 3, wherein the content of Tramadol-HCl is 2 to 60% by weight of the total weight of the tablet.

8. The multilayered tablet of claim 7, wherein the content of Tramadol-HCl is 5 to 45% by weight of the total weight of the tablet.

9. The multilayered tablet of claim 8, wherein the content of Tramadol-HCl is 10 to 35% by weight of the total weight of the tablet.

10. The multilayered tablet according to claim 4, wherein the content of Diclofenac-Na is 2 to 30% by weight of the total weight of the tablet.

11. The multilayered tablet according to claim 10, wherein the content of Diclofenac-Na is 5 to 25% by weight of the total weight of the tablet.

12. The multilayered tablet according to claim 11, wherein the content of Diclofenac-Na is 6 to 20% by weight of the total weight of the tablet.

13. The multilayered tablet according to claim 1, wherein at least one of the Tramadol layer and the Diclofenac layer has a thickness of 0.05 mm to 5 mm.

14. The multilayered tablet according to claim 13, wherein at least one of the Tramadol layer and the Diclofenac layer has a thickness of 0.1 mm to 4 mm.

15. The multilayered tablet according to claim 14, wherein at least one of the Tramadol layer and the Diclofenac layer has a thickness of 1 mm to 3 mm.

16. The multilayered tablet according to claim 1, wherein at least one of the Tramadol layer and the Diclofenac layer is composed of a controlled release matrix.

17. The multilayered tablet according to claim 16, wherein the controlled release matrix comprises a polymer, a wax, a fat, a fatty acid, a fatty alcohol or a corresponding ester or ether, or a mixture thereof.

18. The multilayered tablet according to claim 17, wherein the controlled release matrix comprises a polymer selected from the group consisting of cellulose ethers, a cellulose esters and acrylic resins.

19. The multilayered tablet of claim 18, wherein the polymer is ethylcellulose, hydroxyethylcellulose, hydroxypropylcellulose, or hydroxypropylmethylcellulose.

20. The multilayered tablet of claim 17, wherein the controlled release matrix comprises a fat selected from the group consisting of monoglycerides and diglycerides of $C_{12}$–$C_{30}$ fatty acids.

21. The multilayered tablet of claim 17, wherein the controlled release matrix comprises a $C_{12}$–$C_{30}$ fatty alcohol.

22. The multilayered tablet according claim 1, wherein the Tramadol or Diclofenac or pharmaceutically acceptable salt thereof is formulated into granules, microcapsules or pellets.

23. The multilayered tablet of claim 22, wherein the pellet is produced by extrusion or spheronisation.

24. The multilayered tablet according to claim 1, wherein the separating layer has a layer thickness of 0.05 mm to 10 mm.

25. The multilayered tablet according to claim 24, wherein the separating layer has a layer thickness of 0.1 mm to 5 mm.

26. The multilayered tablet according to claim 25, wherein the separating layer has a layer thickness of 0.15 mm to 3 mm.

27. The multilayered tablet according to claim 1, wherein the separating layer comprises a pharmaceutically acceptable material that is impermeable or only slightly permeable to Tramadol and Diclofenac, and that has a melting point of $\geq 40°$ C.

28. The multilayered tablet according to claim 27, wherein the pharmaceutically acceptable material is selected from the group consisting of polymers, waxes, fats, fatty acids, fatty alcohols, corresponding ethers, and corresponding bases.

29. The multilayered tablet according to claim 28, wherein the pharmaceutically acceptable material comprises a polymer selected from the group consisting of cellulose acetate, cellulose butyrate, polyethylene and ethylene/vinyl acetate copolymer.

30. The multilayered tablet according to claim 1, wherein the separating layer comprises material permeable to the active substance Tramadol or Diclofenac, but the separating layer is so thick that the active substance cannot pass through the separating layer before the active substance outside the separating layer has been completely released.

31. The multilayered tablet according to claim 30, wherein the permeable material is selected from the group consisting of cellulose ethers, cellulose esters and acrylate resins.

32. The multilayered tablet according to claim 31, wherein the permeable material is selected from the group consisting of ethylcellulose, hydroxypropylcellulose, hydroxymethylcellulose, hydroxymethylpropylcellulose, poly(meth)acrylic acid, and derivatives thereof selected from the group consisting of salts, amides and esters.

33. The multilayered tablet according to claim 1, wherein at least one of the separating layer, the Tramadol layer and the Diclofenac layer further comprises an auxiliary substance.

34. The multilayered tablet according to claim 33, wherein the auxiliary substance is selected from the group consisting of fillers, slip agents, lubricants and flow regulating agents.

35. The multilayered tablet according to claim 1, further comprising a coating.

36. The multilayered tablet according to claim 35, wherein the coating is a delayed release coating.

37. The multilayered tablet according to claim 35, wherein the coating is comprised of a water-insoluble polymer or wax.

38. The multilayered tablet according to claim 37, wherein the coating is comprised of a water-insoluble polymer selected from the group consisting of polyacrylic resins and cellulose derivatives selected from the group consisting of cellulose ethers and cellulose esters.

39. The multilayered tablet according to claim 38, wherein the coating is comprised of an alkylcellulose.

40. The multilayered tablet according to claim 38, wherein the coating is comprised of at least one water soluble polymer selected from the group consisting of ethylcellulose and poly(meth)acrylate.

41. The multilayered tablet according to claim 1, wherein more than 70% of the Tramadol and more than 60% of the Diclofenac are released within 16 hours.

42. The multilayered tablet according to claim 41, wherein more than 70% of the Tramadol and more than 60% of the Diclofenac are released within 8 hours.

43. The multilayered tablet according to claim 1, further comprising a release layer that effects the dissociation of the different layers from one another on contact with aqueous body fluids.

44. The multilayered tablet according to claim 1, wherein the tablet has at least one score mark that enables the tablet to be subdivided to administer a fractional dose.

45. The multilayered tablet according to claim 44, wherein the score mark enables the tablet to be halved.

* * * * *